(12) United States Patent
Srigiridhar et al.

(10) Patent No.: US 9,963,476 B2
(45) Date of Patent: May 8, 2018

(54) ANTIOXIDANT COMPOUND HAVING ANTI ATHEROSCLEROTIC EFFECT AND PREPARATION THEREOF

(71) Applicant: Council of Scientific and Industrial Research, New Delhi (IN)

(72) Inventors: Kotamraju Srigiridhar, Hyderabad (IN); Karnewar Santosh, Hyderabad (IN); Vasamsetti Sathish Babu, Hyderabad (IN); Togapur Pavan Kumar, Hyderabad (IN); Basi Venkata Subba Reddy, Hyderabad (IN); Jerald Mahesh Kumar, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days. days.

(21) Appl. No.: 15/443,538

(22) Filed: Feb. 27, 2017

(65) Prior Publication Data
US 2017/0240577 A1    Aug. 24, 2017

Related U.S. Application Data

(62) Division of application No. 15/047,872, filed on Feb. 19, 2016, now Pat. No. 9,580,452.

(30) Foreign Application Priority Data

Feb. 19, 2015 (IN) .............................. 478/DEL/2015

(51) Int. Cl.
C07F 9/655 (2006.01)
(52) U.S. Cl.
CPC ................................ C07F 9/65522 (2013.01)
(58) Field of Classification Search
None
See application file for complete search history.

(56) References Cited

U.S. PATENT DOCUMENTS

| | | | |
|---|---|---|---|
| 4,230,624 | A | 10/1980 | Le Corre et al. |
| 4,977,276 | A | 12/1990 | Berlin et al. |
| 6,331,532 | B1 | 12/2001 | Murphy et al. |
| 9,580,452 | B2 | 2/2017 | Srigiridhar et al. |
| 2016/0244470 | A1 | 8/2016 | Srigiridhar et al. |

FOREIGN PATENT DOCUMENTS

| | | |
|---|---|---|
| WO | WO-9631206 A2 | 10/1996 |
| WO | WO-2008145116 A2 | 12/2008 |
| WO | WO-2011115819 A2 | 9/2011 |

OTHER PUBLICATIONS

"U.S. Appl. No. 15/047,872, Non Final Office Action dated Jul. 5, 2016", 7 pgs.
"U.S. Appl. No. 15/047,872, Notice of Allowance dated Oct. 31, 2016", 7 pgs.
"U.S. Appl. No. 15/047,872, Response filed Jun. 7, 2016 to Restriction Requirement dated Apr. 13, 2016", 6 pgs.
"U.S. Appl. No. 15/047,872, Response filed Sep. 28, 2016 to Non-Final Office Action dated Jul. 5, 2016", 7 pgs.
"U.S. Appl. No. 15/047,872, Restriction Requirement dated Apr. 13, 2016", 7 pgs.
Ballinger, Scott W., et al., "Mitochondrial Integrity and Function in Atherogenesis", Circulation, 106, (2002), 544-549.
Egan, Denise, et al., "The Pharmacology, Metabolism, Analysis, and Applications of Coumarin and Coumarin-Related Compounds", Drug Metabolism Reviews, 22(5), (1990), 503-529.
Espey, Michael G., et al., "Focusing of nitric oxide mediated nitrosation and oxidative nitrosylation as a consequence of reaction with superoxide", Proc. Natl. Acad. Sci. USA, 99(17), (2002), 11127-11132.
Kaneko, Takao, et al., "Protection of coumarins against linoleic acid", Chemico-Biological Interactions, 142, (2003), 239-254.
Kelso, Geoffrey F., et al., "Selective Targeting of a Redox-active Ubiquinone to Mitochondria within Cells", The Journal of Biological Chemistry, 276(7), (2001), 4588-4596.
Lin, Wea-Lung, et al., "Inhibitory effect on esculetin on oxidative damage induced by t-butyl hydroperoxide in rat liver", Arch Toxicol, 74, (2000), 467-472.
Mugabo, Yves, et al., "Palmitate induces C-reactive protein expression in human aortic endothelial cells. Relevance to fatty acid-induced endothelial dysfunction", Metabolism Clinical and Experimental, 60, (2011), 640-648.
Murphy, Michael P., et al., "Drug delivery to mitochondria: the key to mitochondrial medicine", Advanced Drug Delivery Reviews, 41, (2000), 235-250.
Tarpey, Margaret M., et al., "Methods for detection of reactive metabolites of oxygen and nitrogen: in vitro and in vivo considerations", Am. J. Physiol. Regul. Integr. Comp. Physiol., 286(3), (2004), R431-R444.

Primary Examiner — Heidi Reese
(74) Attorney, Agent, or Firm — Schwegman Lundberg & Woessner, P.A.

(57) ABSTRACT

The present invention relates to an antioxidant compound having anti atherosclerotic effect and preparation thereof. The present invention more particularly relates to the synthesis of TPP+ coupled esculetin (mitochondria-targeted esculetin [Mito-Esc]) followed by the biological evaluation of Mito-Esc for its ability to attenuate Angiotensin-II-induced atherosclerosis in apolipoproteinE knockout (ApoE$^{-/-}$ mice along with the endothelial cell age-delaying effects of Mito-Esc.

1 Claim, 9 Drawing Sheets

Control p16  Mito-Esc p16
(p10-p16)   (p10-p16)

FIG. 6B

Control     $H_2O_2$     Mito-Esc     Mito-Esc + $H_2O_2$ p8

FIG. 7A ■ control □ Ang-II ⊠ Ang-II+ Mito-Esc

FIG. 7D  Control    Ang-II    Mito-Esc + Ang-II

Mason-Trichome

ANTIOXIDANT COMPOUND HAVING ANTI ATHEROSCLEROTIC EFFECT AND PREPARATION THEREOF

CROSS-REFERENCE TO RELATED APPLICATIONS

This application is a divisional and claims the benefit of priority of U.S. application Ser. No. 15/047,872, filed 19 Feb. 2016, which claims the benefit of priority to India Application No. 478/DEL/2015, filed 19 Feb. 2015, which applications are incorporated herein by reference and made a part hereof in their entirety, and the benefit of priority of each of which is claimed herein.

FIELD OF INVENTION

The present invention relates to an antioxidant compound having anti atherosclerotic effect and preparation thereof. The present invention relates to the synthesis of TPP+ coupled esculetin (mitochondria-targeted esculetin [Milo-Esc]) followed by the biological evaluation of Mito-Esc for its ability to attenuate Angiotensin-II-induced atherosclerosis in apolipoproteinE knockout (ApoE$^{-/-}$) mice along with the endothelial cell age-delaying effects of Mito-Esc.

BACKGROUND AND PRIOR ART REFERENCES

Atherosclerosis is an excessive inflammatory/proliferative response of the vascular wall to various forms of injury. It has been suggested that, during inflammation, reactive oxygen (ROS) and reactive nitrogen species (RNS)-induced endothelial cell damage represent an important primary event in the process of atherosclerotic lesion formation. The resulting oxidative and nitrosative stress impairs the critical balance of the availability of endothelium-derived nitric oxide in turn promoting the proinflammatory signaling events, ultimately leading to the plaque formation. Atherosclerosis initiating events may be different under different conditions; however endothelial dysfunction is known to be one of the major initiating events. Macrophages also undergo apoptosis inside the endothelium, leading to their phagocytic clearance.

Increased mitochondrial oxidative damage is a major feature of most age-related human diseases including atherosclerosis and abnormal electron leakage from mitochondria in the respiratory chain in oxidant-stressed cells triggers the formation of ROS in mitochondria leading to altered behavior of the cell/cell death. Previously many studies have linked excess generation of ROS with vascular lesion formation and functional defects. More so, a role for mitochondria-derived ROS in atherogenesis is supported by links between common risk factors for coronary artery disease and increased levels of ROS. Mitochondrial ROS is increased in response to many atherosclerosis inducers including hyperglycemia, triglycerides and ox-LDL. Aortic samples from atherosclerotic patients had greater mitochondrial DNA (mtDNA) damage than nonatherosclerotic aortic samples from age-matched transplant donors (Mitochondrial integrity and function in atherogenesis. Circulation. 2002; 106:544-549). Even though endothelial cells have low mitochondria content, mitochondrial dynamics acts as a prime orchestrator of endothelial homeostasis under normal conditions, an impairment of mitochondrial dynamics because of excess ROS production would cause endothelial dysfunction resulting in diverse vascular diseases. Exposure of endothelial cells to free fatty acids, a common feature seen in patients with metabolic syndrome increases mitochondrial ROS (Palmitate induces C-reactive protein expression in human aortic endothelial cells. Relevance to fatty acid-induced endothelial dysfunction. Metabolism. (2011) 60: 640-648).

Therefore keeping in view of the involvement of mitochondrial ROS in causing endothelial dysfunction leading to the accentuation of vascular diseases, it would be ideal to counteract mitochondria ROS by targeting ROS scavengers specifically to the site of action. The major drawback of antioxidant therapy in the treatment of mitochondrial diseases has been the inability to enhance antioxidant levels in mitochondria. Recently, there was a breakthrough in mitochondrial targeting of antioxidants (Drug delivery to mitochondria: the key to mitochondrial medicine. Adv Drug Deliv Rev. (2000) 41: 235-50). Antioxidants were covalently coupled to a triphenylphosphonium cation (TPP$^+$), and these compounds were preferentially taken up by mitochondria (Selective targeting of a redox-active ubiquinone to mitochondria within cells: antioxidant and antiapoptotic properties. J Biol Chem. (2001) 276: 4588-4596). The lipophilic cations easily permeate through the lipid bilayers and subsequently build up several hundred-fold within mitochondria because of a large mitochondrial membrane potential. The uptake of lipophilic cations into the mitochondria increases 10-fold for every 61.5 mV difference in the membrane potential, leading to a 100- to 500-fold accumulation in mitochondria. This strategy not only reduces the concentration of the molecule that is being employed to scavenge ROS, but also reduces the non-specific effects of the molecule if it were to be used at high concentrations to elicit a similar effect.

Coumarins constitute a group of phenolic compounds widely distributed in natural products (The Pharmacology, Metabolism, Analysis and Applications of Coumarin and Coumarin-Related Compounds. Drug Metab Rev (1990) 22: 503-529), and they have recently attracted much attention because of their wider pharmacological activities. Of these, esculetin (6,7-dihydroxycoumarin) has been shown to be a lipoxygenase inhibitor, and it inhibits the production of leukotrienes and hydroxyeicosatetraenoic acid through the lipoxygenase pathway. More recently, esculetin has been reported to inhibit oxidative damage induced by tert-butyl hydroperoxide in rat liver (Inhibitory effect of esculetin on oxidative damage induced by t-butyl hydroperoxide in rat liver. Arch Toxicol. (2000) 74:467-72). Esculetin protects against cytotoxicity induced by linoleic acid hydroperoxide in HUVEC cells and the radical scavenging ability of esculetin was confirmed by electron para magnetic resonance spectroscopy (Protection of coumarins against linoleic acid hydroperoxide-induced cytotoxicity. Chemico-Biological Interactions 142 (2003) 239-254). However, as coumarins may have poor bioavailability in vivo and do not significantly accumulate within mitochondria, their effectiveness remains limited and because of this, they may have to be employed in higher concentrations to scavenge mitochondrial ROS. In the present patent application, we have used lipophilic cation (TPP+) to target esculetin (FIG. X) to mitochondria and show that mitochondria-targeted esculetin (Mito-Esc) protects oxidant-induced endothelial cell death via nitric oxide and AMPK-dependent pathways at far below concentrations than reported earlier with native esculetin and further we report that Mito-Esc significantly inhibits aortic aneurysm (AA) and atheromatous plaque formation in Angiotensin-II-induced atherosclerotic process in Apolipoprotein E$^{-/-}$ mice model. The following are the prior art literature related to the present invention (WO1996031206; U.S. Pat. No. 6,331,532; WO2008145116; U.S. Pat. No. 4,977,276; U.S. Pat. No. 4,230,624; WO2011115819).

OBJECTIVES OF THE INVENTION

The main objectives of the invention are as follows
1) To synthesize triphenylphosphonium cation (TPP+) coupled esculetin (Mito-Esc) and compare the accumulation of Mito-Esc versus native esculetin in mitochondria.
2) To study the effect of Mitochondria-targeted esculetin (Mito-Esc) during oxidative stress-induced endothelial cell death.
3) To study the age-delaying effects of Mito-Esc in human aortic endothelial cells (HAEC).
4) To understand the mechanisms of Mito-Esc in regulating oxidative stress-induced endothelial cell death.
5) To investigate the effects of Mito-Esc administration during angiotensin-II (Ang-II)-induced atherosclerosis in Apolipoprotein E knockout (ApoE$^{-/-}$) mice model.

SUMMARY OF THE INVENTION

Accordingly the present invention provides an antioxidant compound having anti atherosclerotic effect and preparation thereof. The invention relates to the synthesis of TPP+ coupled esculetin compound (mitochondria-targeted esculetin (Mito-Esc)) of formula 1, following the scheme as shown in scheme 1

X=Carbon chain of 1-30
Z=halogen
R=H/one or more than one substitution alkyl/aryl/heteroatom The biological evaluation of Mito-Esc for its ability to attenuate Angiotensin-II-induced atherosclerosis in ApoE$^{-/-}$ mice has been done. Mito-Esc selectively accumulated in the mitochondria compared to native (un-tagged) esculetin. Mito-Esc at very low concentrations (2.5 μM) protected human aortic endothelial cells (HAEC) from $H_2O_2$ or Angiotensin-II induced oxidative stress and cell death. Mito-Esc by upregulating nitric oxide (NO) levels via increased phosphorylations of both AMPK and eNOS protected HAEC from oxidant-induced cell death. Furthermore, Mito-Esc reduced $H_2O_2$-induced endothelial cell aging. In vivo experimentations in ApoE-/- mice revealed that administration of Mito-Esc in drinking water for 45 days significantly attenuated Ang-II-induced atherosclerosis by reducing plaque and aortic aneurysm incidence. Mito-Esc also significantly inhibited Ang-II-induced proinflammatory cytokines production along with the reduction in the levels of serum cholesterol, LDL and triglycerides while increasing the HDL levels. Taken together, it is concluded that Mito-Esc greatly protects oxidant-induced endothelial cell death and atherosclerosis in ApoE$^{-/-}$ mice by modulating intracellular pathways regulating nitric oxide levels and inflammatory cascades, indicating that the formula 1 is an antioxidant compound.

BRIEF DESCRIPTION OF DRAWINGS

FIGS. 1A and 1B. Mitochondria-targeted esculetin (Mito-Esc) but not esculetin protects endothelial cells from $H_2O_2$ and Ang-II-induced cell death in human aortic endothelial cells (HAEC). Cells were treated with Mito-Esc or Esc (2.5 μM) for 24 h.

FIGS. 2A and 2B. Mitochondria-targeted esculetin (Mito-Esc) restores $H_2O_2$-induced mitochondrial membrane depolarization in HAEC. Cells were treated with Mito-Esc (2.5 μM) for 16 h.

Scheme I

Synthesis

FIGS. 3A through 3F. Mito-Esc induced nitric oxide generation is mediated by increased eNOS phosphorylation in HAEC. In FIG. 3A cells were treated with $H_2O_2$ (500 µM) in the presence or absence of Mito-Esc (2.5 µM) or esculetin (2.5 µM) for a period of 8 h and nitric oxide levels were measured by employing DAF-2A as described in the experimental section.

FIGS. 4A through 4C. Effect of Mito-Esc on AMPK phosphorylation in endothelial cells.

FIGS. 5A through 5E. Mito-Esc increases mitochondrial biogenesis in HAEC through the upregulation of SIRT3, PGC-1α and TFAM in endothelial cells.

FIGS. 6A and 6B. Mito-Esc delays endothelial cell aging and also inhibits oxidative stress-induced cell senescence.

FIGS. 7A through 7E. Mito-Esc administration inhibits Ang-II induced atherosclerosis in ApoE$^{-/-}$ mice aorta.

FIGS. 9A through 9E. Mito-Esc administration inhibits Ang-II induced proinflammatory cytokines production in ApoE$^{-/-}$ mice.

DETAILED DESCRIPTION OF THE INVENTION

Procedure for the Synthesis of Compound C:

Compound B (0.505 mL, 3.77 mmol) was taken in dry THF (10 mL) under nitrogen atmosphere and the temperature was cooled to −75 to −80° C. A solution of LDA (2 M in THF, 3.77 mL, 7.54 mmol) was added slowly to the reaction mixture at −78° C. and the resulting mixture was stirred for 1 h. A solution of compound A (1 g, 3.77 mmol) in dry THF (10 mL) was cooled to −78° C. in another flask. A solution of t-butyl lithiate B was added to compound A slowly at −78° C. and the resulting mixture was stirred at the same temperature for 1 h. The reaction progress was monitored by TLC. After completion, the reaction mixture was quenched with water (10 mL) and extracted with ethyl acetate (3×20 mL), the combined organic extracts were washed with water (20 mL) and dried over anhydrous $Na_2SO_4$ filtered and concentrated under vacuum to afford the crude product (1.2 g) as colorless oil. The crude product was directly used as such in next step without any purification.

Procedure for the Synthesis of Compound E:

A mixture of compound 3 (2.6 g, crude, 7.761 mmol) and compound D (1.95 g, 7.761 mmol) in 75% aqueous $H_2SO_4$ (26 mL) was stirred at RT for 18-20 h. The reaction progress was monitored by TLC. After completion, the reaction mixture was diluted with water (50 mL) and extracted with ethyl acetate (2×25 mL). The combined organic extracts were washed with water and dried over $Na_2SO_4$, filtered and concentrated under vacuum to obtain crude compound. The crude product was purified by flash column chromatography (Silica gel: 100-200 mesh) eluting with 50% ethyl acetate in hexane to afford the desired compound 5 (300 mg, Yield: 22%) as pale yellow solid.

$^1$H NMR (400 MHz, DMSO-d6): δ1.31-1.37 (m, 8H), 1.57-1.61 (m, 2H), 1.77-1.80 (m, 2H), 2.67-2.63 (t, 2H, J=7.6 Hz), 3.53-3.50 (t, 2H, J=6.6 Hz), 6.05 (s, 1H), 6.73 (s, 1H), 7.04 (s, 1H), 9.12 (br, 1H), 10.4 (br, 1H). LCMS Purity: 93.88%, 371.15 (M+H).

Procedure for the Synthesis of Esucletin Analogue F:

To a stirred solution of compound E (140 mg, 0.379 mmol) in dry DMF (5 mL) was added TPP (99 mg, 0.379 mmol) and the resulting mixture was heated to 150-170° C. for 5-8 h. The progress of the reaction was monitored by TLC. After completion of the reaction, DMF was distilled off completely under reduced pressure to obtain crude compound. The crude product was washed several times with ethyl acetate and diethyl ether to afford the esucletin analog F (Yield: 140 mg, 57.8%) as pale brown solid.

$^1$H NMR (400 MHz, CD$_3$OD): δ1.34-1.42 (m, 6H), 1.53-1.56 (m, 2H), 1.61-1.69 (m, 4H), 2.68-2.72 (t, 2H, J=7.6 Hz), 3.34-3.41 (m, 2H), 6.04 (s, 1H), 6.74 (s, 1H), 7.07 (s, 1H), 7.72-7.89 (m, 15H). LCMS Purity: 88.99%, 551 (M-Br).

Endothelial Cell Experiments.

Human aortic endothelial cells (HAECs) were obtained from ATCC (Manassas, Va.) and maintained (37° C. 5% CO$_2$) in basal medium supplemented with 10% FBS, VEGF (5 ng/mL), hEGF (5 ng/mL), hFGF (5 ng/mL), IGF-1 (15 ng/mL), ascorbic acid (50 µg/mL), hydrocortisone (1 µg/mL), amphotericin (15 ng/mL), gentamicin (30 ng/mL) and heparin (0.75 Units/mL). Cells used in this study were between passages 4 and 9. Esculetin, Mito-Esc, TPP and nitric oxide synthase inhibitor (L-NAME) were added 2 h before the addition of H$_2$O$_2$ or Ang-II.

Animal Experiments.

Experiments were conducted in 2-month-old male apolipoprotein E knockout (ApoE$^{-/-}$) mice according to the guidelines formulated for care and use of animals in scientific research (ICMR, New Delhi, India) at a CPCSEA (Committee for the Purpose of Control and Supervision of Experiments on Animals) registered animal facility. The experimental protocols were approved by the Institutional Animal Ethical Committee at CSIR-IICT (IICT/CB/SK/20/12/2013/10). Animals were randomly divided into 3 groups each n=7:1) control 2) Ang-II treatment and 3) Mito-Esculetin+Ang-II treatment. Ang-II and Mito-Esculetin treatment groups received Ang-II (sigma) at a dose of 1.44 mg/kg/day for 6 weeks through sub-cutaneous route where as control group received normal saline. Mito-Esculetin treatment group received the compound at a dose of 0.5 mg/kg/day in normal drinking water. All animals were fed on normal chow throughout the study. After 6 weeks, all groups of animals were sacrificed as per standard protocols for euthanasia.

Trypan Blue Cell Viability Assay.

At the end of the treatments, cells were harvested and re-suspended in 0.4% trypan blue (Life Technologies) and percent cell viability was counted using cell countess chamber (Life Technologies).

Caspase Activity.

At the end of the treatments. HAEC were washed twice with cold DPBS and lysed in buffer containing 10-mM Tris-HCl, 10-mM NaH$_2$PO$_4$/Na$_2$HPO$_4$ (pH, 7.5). 130-mM NaCl. 1% Triton, and 10-mM sodium pyrophosphate. Cell lysates were incubated with either with caspase-3 fluorogenic substrate (N-acetyl-Asp-Glu-Val-Asp-7-amido-4-methylcoumarin) or caspase-8 fluorogenic substrate (N-acetyl-Ileu-Glu-Thr-Asp-7 amido-4-methylcoumarin) at 37° C. for 1 h. The 7-amido-4-methyl-coumarin liberated was measured in a multi mode reader (PerkinElmer) with λex=380 nm and λem=460 nm.

Measurement of H$_2$O$_2$ Levels.

Amplex red reagent was used to detect the released H$_2$O$_2$ from cells. At the end of the treatments, HAECs were trypsinized and 20,000 cells were resuspended in 100 µl of Kreb's ringer phosphate buffer (pH, 7.35) and the assay was initiated by mixing with 100 µl of Krebs-Ringer buffer solution containing 50 µM amplex red reagent along with 0.1 U/mL horseradish peroxidase (HRP). Immediately, formation of resorufin fluorescence was measured in multi mode reader (PerkinElmer) with λex=540 and λem=585.

Detection of Mitochondrial Transmembrane Potential Changes.

Mitochondrial potential was assessed by using the fluorescent potentiometric JC-1 dye. In healthy cells, JC-1 forms J-aggregates that display a strong red fluorescence with excitation of 560 nm and emission wavelength at 595 nm. In apoptotic or unhealthy cells, JC-1 exists as monomers that display a strong green fluorescence with excitation and emission at 485 nm and 535 nm, respectively. At the end of the treatments, cells were washed with Dulbeccos phosphate buffer solution (DPBS) and incubated with JC-1 dye (5 mg/ml) for 20 min. Cells were again washed twice with DPBS and maintained in culture medium. Fluorescence was monitored by using Olympus fluorescence microscope with Rhodamine and Fluorescein isothiocyanate (FITC) filters.

Measurement of Intracellular Nitric Oxide Levels.

Intracellular nitric oxide levels were monitored by using the Diaminofluorescein-diacetate (DAF-2DA) fluorescence probe. After the treatments, cells were washed with DPBS and incubated in fresh culture medium without fetal bovine serum (FBS). DAF-2DA was added at a final concentration of 5 µM, and the cells were incubated for 30 minutes. The cells were washed twice with DPBS and maintained in culture medium. Fluorescence was monitored by using Olympus fluorescence microscope with FITC filter (λex=488 nm and λem=610 nm). Fluorescence intensity was calculated by Image-Pro plus7.0 software.

Mitotracker Staining.

Mitochondrial content in cells was assessed by selectively loading the mitochondria with the red fluorescent dye Mitotracker (Invitrogen, Carlsbad, Calif.).

Western Blot Analysis.

At the end of the treatments, HAECs were washed with ice-cold DPBS and resuspended in RIPA buffer (20 mM Tris-HCl, pH 7.4/2.5 mM EDTA/1% Triton X-100/1% sodium deoxycholate/1% SDS/100 mM NaCl/100 mM sodium fluoride) containing protease inhibitor cocktail and phosphatase inhibitor cocktail-2 and -3. The lysate was centrifuged for 15 min at 12000×g. Proteins were resolved on 8% SDS-PAGE and blotted onto nitrocellulose membrane and probed with rabbit anti-p-eNOS (ser-1177), rabbit anti-eNOS, rabbit anti-p-AMPK-1α (Thr-172) and rabbit anti-AMPK antibodies and then incubated with horseradish peroxidase-conjugated goat anti-rabbit IgG secondary antibody (1:5000). Protein bands were detected by using HRP substrate (Millipore-luminata). All the antibodies used for this study were from CST.

Isolation of Cytosolic and Mitochondrial Fractions from HAEC's and Apo E$^{-/-}$ Mice Aortic Tissue.

HAECs were grown in 90-mm dishes, treated with or without Mito-Esculetin (2.5 µM) for 24 h. After the treatment, cells were washed thrice with PBS. Similarly Mito-Esculetin+ Ang-II treatment group, Ang-II alone treatment group and control Apo E$^{-/-}$ mice aortic tissue was taken. The isolation of mitochondrial and cytosolic extracts was carried out using a commercially available Proteo Extract Cytosol/Mitochondria Fractionation Kit (Cat. no. QIA88-Merck, USA) according to manufacturer's instructions.

Measurement of Mitochondrial Bioenergetics.

The oxygen consumption rate (OCR) and extracellular acidification rates in HAEC treated with Mito-Esculetin (2.5 uM) for 24 h was measured using Seahorse XF24-extracellular flux analyzer (Seahorse Biosciences, North Billerica Mass.) according to the manufacturer's protocol.

β-Galactosidase (β-Gal) Staining.

Low and high passage number (which reflects young and aged) endothelial cells (HAEC) cells were treated with various concentrations of $H_2O_2$ (50-500 µM)) for 8 h. Cells were washed in PBS, fixed for 3-5 mM (room temperature) in 2% formaldehyde/0.2% glutaraldehyde, washed, and incubated at 37° C. with fresh senescence associated β-Gal (SA-,β-Gal) stain solution: 1 mg of 5-bromo-4-chloro-3-indolyl β-D-galactoside (X-Gal) per ml (stock=20 mg of dimethylformamide per ml)/40 mM citric acid/sodium phosphate, pH 6.0; 5 mM potassium ferrocyanide/5 mM potassium ferricyanide/150 mM NaCl/2 mM $MgCl_2$. Staining was visualized after 24 h using a phase contrast microscope. Detection and Quantification of Mito-Esc by Mass Spectrometry.

Initially, mitochondrial and cytosolic fractions were separated using a commercially available kit as mentioned elsewhere. Mito-Esc was quantified in the mitochondrial and cytosolic fractions obtained from HAEC and aorta of ApoE$^{-/-}$ mice of different treatment groups as mentioned in Animal Experiments section (Table-1). Electrospray ionization (ESI)-MS. ESI-MS (positive mode) measurements were performed using a quadrupole time-of-flight mass spectrometer (QSTAR XL, Applied Biosystems/MDS Sciex, Foster City, Calif., USA). The data acquisition was under the control of Analyst QS software (Applied Biosystems). For the CID (collision-induced dissociation) experiments, the precursor ions were selected using the quadrupole analyzer and the product ions were analyzed using the TOF analyzer.

The detailed description of these inventions is explained with following examples but these should not construe to limit the invention.

Example 1

Mitochondria-Targeted Esculetin (Mito-Esc) but not Native Esculetin Abrogates Oxidant-Induced Cell Death in Human Aortic Endothelial Cells (HAEC)—

Figures 1A, 1B:
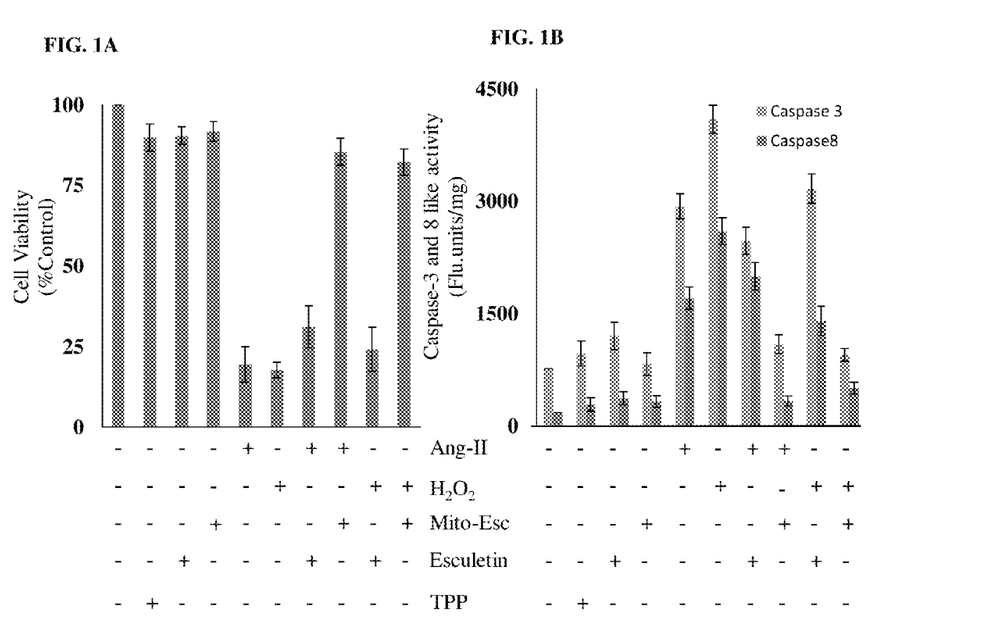
FIG. 1A shows the cell viability by trypan blue assay and FIG. 1B shows the caspase-3 and -8 activation.

We have studied the effects of mitochondria-targeted esculetin (Mito-Esc) (2.5 µM) as well as the native esculetin (2.5 µM) on Ang-II (500 nM) and $H_2O_2$ (500 µM)-induced endothelial cell death. For this, cells were pretreated for 2 h with either Mito-Esc or esculetin before they were incubated with either $H_2O_2$ or Ang-II. Mito-Esc but not esculetin significantly inhibited oxidant ($H_2O_2$ and Ang-II)-induced endothelial cell death (FIG. 1C). However, TPP$^+$ alone did not have any appreciable cytotoxic/cytoprotective effect in HAEC (FIG. 2C). Thereby, indicating that the observed protective effect of Mito-Esc is not because of the TPP$^+$ side chain coupled to esculetin. Next, to confirm that $H_2O_2$ and Ang-II caused an apoptotic mediated cell death in HAEC, we measured caspase-3 and -8 activities in cells treated with same conditions as shown in FIG. 1B. The results showed that Mito-Esc-pretreated cells were markedly resistant to $H_2O_2$ and Ang-II-induced caspase activation, whereas treatment with native esculetin elicited marginal effect on caspase-3 and -8 activation in $H_2O_2$ and Ang-II treated cells as compared to Mito-Esc (FIG. 2D). These results are consistent with the cell death measured by trypan blue dye exclusion method.

Example 2

Mito-Esc Decomposes Ang-II-Induced $H_2O_2$ Generation and Preserves Oxidant Mediated Depolarization of Mitochondrial Membrane Potential—

Figure 2A:
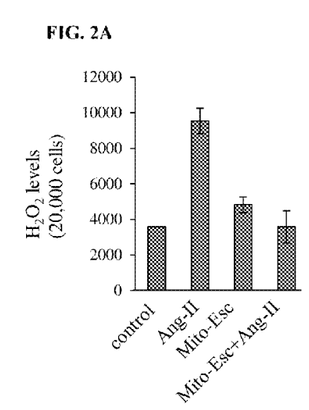
FIG. 2A shows the $H_2O_2$ generation with Ang-II treatment and the effect of Mito-Esc on Ang-II-induced $H_2O_2$ production and FIG. 2B represents the mitochondrial membrane potential measured as described in Experimental section.
Figure 2B:
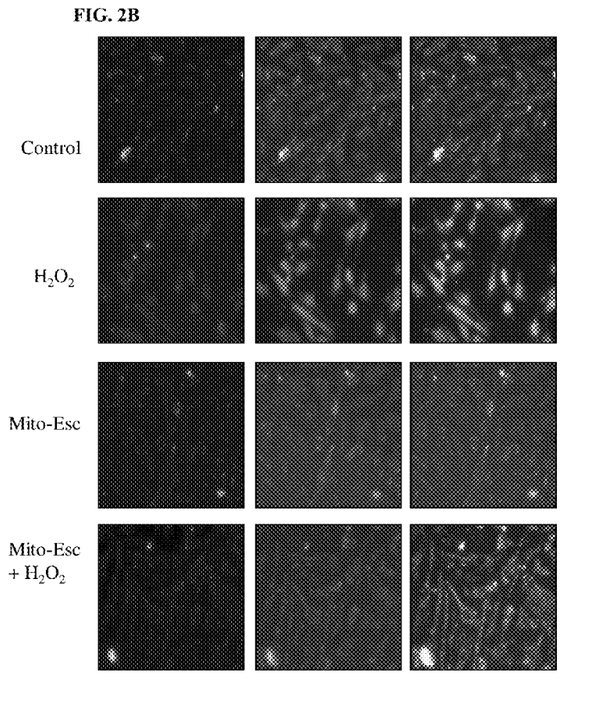
Figure 3A:
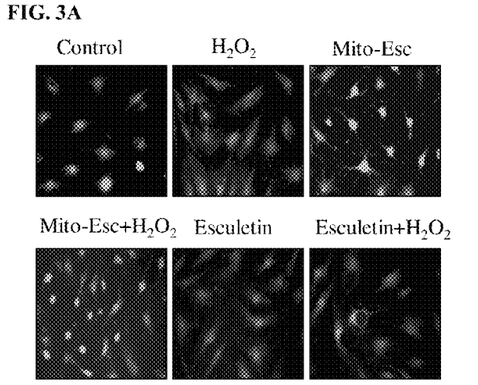
Figure 3B:
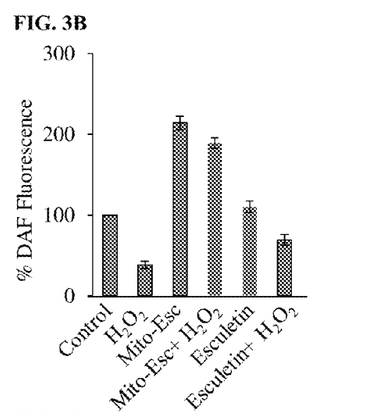
In FIG. 3B and FIG. 3C cells were treated with various concentrations of Mito-Esc (1-5 µM) for 8 h and eNOS and phospho-eNOS protein levels were measured by Western blot analysis as mentioned in the Experimental Section.
Figure 3C:
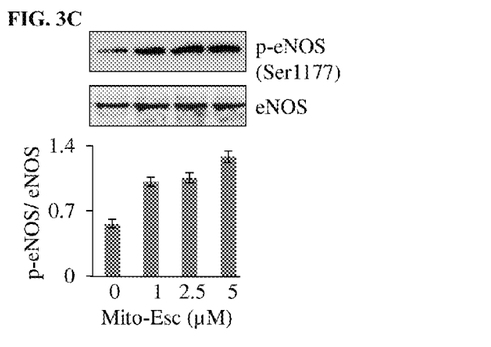
Figure 3D:
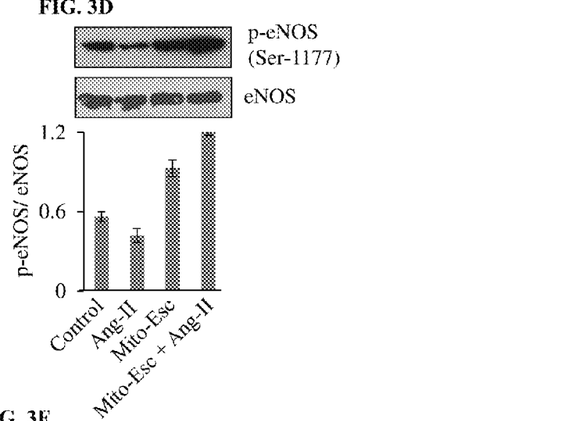
In FIG. 3D cells were treated with Ang-II (500 nM) in the presence or absence of Mito-Esc (2.5 µM) for 8 h and eNOS and phospho-eNOS protein levels were measured.
Figure 3E:
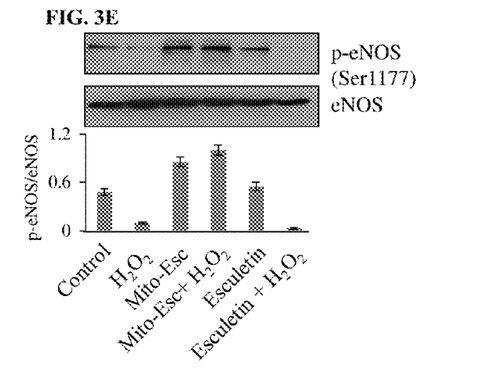
FIG. 3E same as FIG. 3A except that eNOS and phospho-eNOS protein levels were measured by Western blot analysis.
Figure 3F:
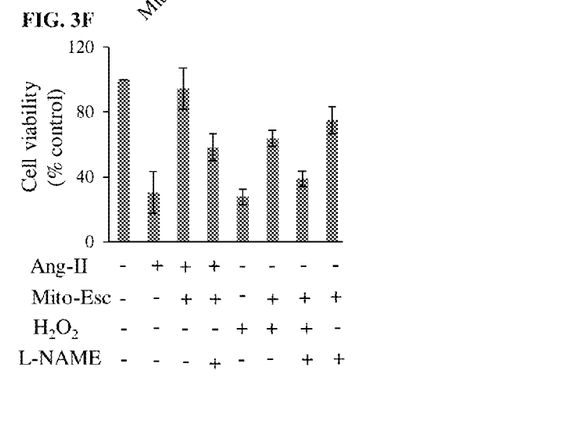
In FIG. 3F cells were treated with either $H_2O_2$ (500 µM) or Ang-II (500 nM) in the presence or absence of either Mito-Esc or L-NAME (2 mM) for 24 h and cell viability was measured by trypan blue exclusion assay as described in Experimental Section.

Ang-II is known to increase oxidative stress through increased production of $H_2O_2$ (Doughan A K, Harrison D G, Dikalov S I. Circ Res (2008) 102:488-96). To see the effect of Mito-Esc in regulating Ang-II-induced $H_2O_2$ production in endothelial cells, HAEC were treated with Ang-II (500 nM) in the presence or absence of Mito-Esc (2.5 µM) for a period of 16 h and $H_2O_2$ production was measured by Amplex red assay. In cells treated with Ang-II, $H_2O_2$ generation was significantly increased by around 2.7 fold compared to untreated conditions (FIG. 2A). Interestingly, Mito-Esc co-treatment completely reversed $H_2O_2$ levels to control conditions (FIG. 3A). Thereby suggesting that Ang-II-induced cytotoxicity in HAEC involves oxidative stress and that co-incubation of HAEC with mito-Esc greatly attenuates Ang-II-mediated cell death by decomposing $H_2O_2$ levels. Further, we assessed the effect of Mito-Esc on $H_2O_2$-induced mitochondrial membrane depolarization. HAEC were treated with $H_2O_2$ (500 µM) in the presence or absence of Mito-Esc for a period of 16 h and mitochondrial membrane potential was measured using a mitochondrial membrane sensor kit. Mito-Sensor is a cationic dye that fluoresces differently in apoptotic and nonapoptotic cells. The Mito-Sensor dye forms aggregates in mitochondria of healthy cells and exhibits a red fluorescence. In apoptotic cells, membrane potentials are altered and the Mito-Sensor dye cannot accumulate in mitochondria and, thus, remain as monomers leading to a green fluorescence. In agreement with the results shown in FIG. 1 and FIG. 2A, Mito-Esc significantly rescued $H_2O_2$-mediated mitochondrial membrane depolarization (FIG. 2B). These results indicate that Mito-Esc by decomposing mitochondria-derived $H_2O_2$, protects endothelial cells during oxidant stress.

Example 3

Mito-Esc Potentiates Nitric Oxide Generation Via Increased eNOS Phosphorylation in HAEC: Effect of NOS Inhibitor on Mito-Esc-Mediated Inhibition of Oxidant Mediated Cell Death—

Figure 4A:
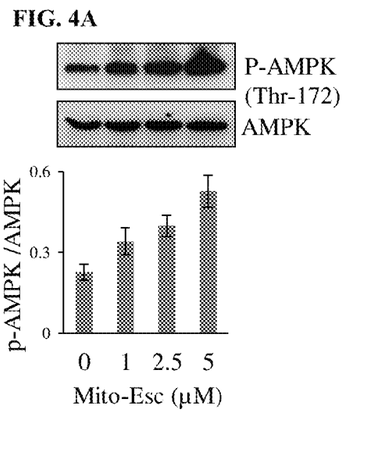
In FIG. 4A, HAEC were treated with various concentrations of Mito-Esc (1-5 µM) for 8 h and AMPK and phospho-AMPK protein levels were measured by Western blot analysis.
Figure 4B:
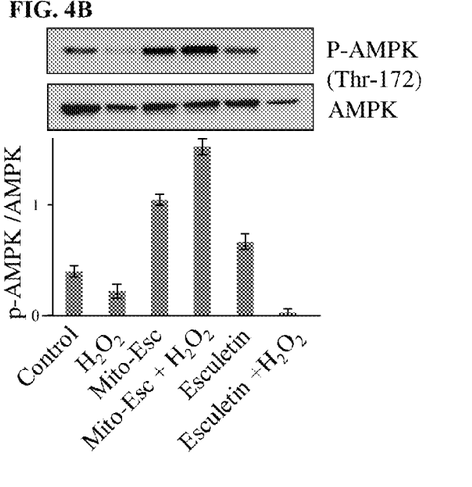
In FIG. 4B, cells were treated with $H_2O_2$ (500 uM) in the presence or absence of either Mito-Esc (2.5 µM) or esculetin (2.5 µM) for 8 h and AMPK and phospho-AMPK protein levels were measured by Western blot analysis.
Figure 4C:
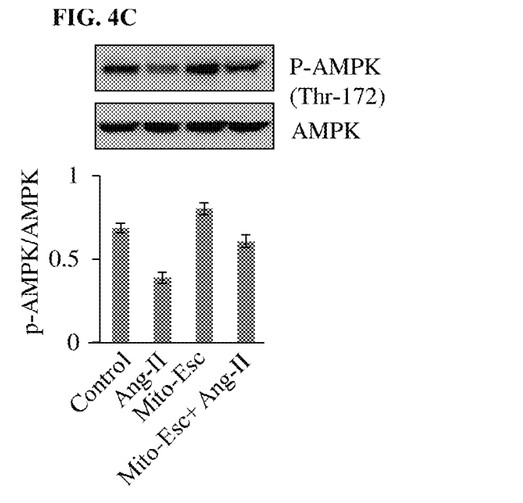
In FIG. 4C, same as FIG. 4B except that cells were treated with Ang-II (500 nM) in the presence or absence of Mito-Esc or esculetin.

To gain mechanistic insight on Mito-Esc-mediated protection of endothelial cells from oxidant-induced endothelial cell death, initially we hypothesized that Mito-Esc may augment intracellular nitric oxide generation. To study this, HAEC were treated with both Mito-Esc and esculetin in the presence or absence of $H_2O_2$ for a period of 4 h and nitric oxide (NO) levels were monitored by DAF-2 derived green fluorescence. Previously, it has been shown that DAF-2 forms a fluorescent triazole-type product in the presence of an oxidant derived from nitric oxide and oxygen interaction (Proc. Natl. Acad. Sci. USA 99: 11127-11132; 2002.; Am. J. Physiol. Regul. Integ. Comp. Physiol. 286:R344-R431; 2004). Intriguingly, Mito-Esc alone but not native esculetin greatly enhanced the DAF-2 fluorescence in HAEC (FIGS. 4A and 4B). Thereby indicating that incubation of endothelial cells with Mito-Esc causes an increase in NO production. Also, Mito-Esc significantly restored $H_2O_2$-mediated depletion of NO levels (FIGS. 4A and 4B). However, under these conditions, native esculetin did not show any noticeable effect on NO generation (FIGS. 4A and 4B). Next, we investigated the possible role of endothelial nitric oxide synthase (eNOS) in mediating the Mito-Esc induced NO generation in HAEC. For this, endothelial cells were treated with various concentrations of Mito-Esc (1-5 µM) for a period of 8 h. Mito-Esc dose-dependently increased the phosphorylation of eNOS at Ser-1177 (FIG. 4C). To further substantiate the results of DAF fluorescence, eNOS phosphorylation was measured in HAEC incubated with either with $H_2O_2$ or Ang-II for 8 h in cells pretreated with Mito-Esc or native esculetin. It was observed that both $H_2O_2$ and Ang-II caused a reduction in Phospho eNOS (Ser-1177) levels (FIG. 4D). Ang-II treatment imposed a drastic inhibition of phospho-eNOS levels when compared to $H_2O_2$ treatment in endothelial cells (FIG. 4D). Under these conditions, however, Mito-Esc but not native esculetin treatment caused cells resistant to oxidant-mediated decrease in eNOS-phosphorylation (FIG. 4D and FIG. 4E). Furthermore, incubation of cells with L-NG-Nitro-L-arginine (L-NAME), a known NOS inhibitor; significantly abrogated Mito-Esc-mediated cyto-protective effects against oxidant-induced cell death (FIG. 4G). Taken together, these results suggest that Mito-Esc mediated increase in nitric oxide generation via increased phosphorylation of eNOS is in part responsible for maintaining endothelial cell viability during oxidative stress.

Example 4

Mito-Esc Mediated Increase in eNOS Phosphorylation and NO Generation is Caused by Increased Activation of AMPK—

Previously, it was shown that AMPK co-immunoprecipitates with cardiac endothelial NO synthase (eNOS) and phosphorylates Ser-1177 in the presence of $Ca^{2+}$-calmodulin (CaM) to activate eNOS both in vitro and during ischaemia in rat hearts (FEBS Lett. (1999) 443:285-289). To test whether Mito-Esc mediates increased phosphorylation of eNOS through AMPK activation, initially, HAEC were treated various concentrations of Mito-Esc (1-5 µM) for 8 h and AMPK1-α phosphorylation (Thr-172) levels were measured. Mito-Esc lead to a dose-dependent increase in phospho-AMPK1-α (Thr-172) levels with maximum effect at 2.5 µM of Mito-Esc (FIG. 4A). Next, we investigated the phospho-AMPK1-α levels in HAEC treated with $H_2O_2$ in the presence or absence of either Mito-Esc or native esculetin. Incubation of cells with either $H_2O_2$ alone or in the presence of native esculetin for 8 h significantly decreased AMPK1-α phosphorylation and whereas incubation of cells with either Mito-Esc alone or in the presence of $H_2O_2$ greatly enhanced the phospho-AMPK1-α levels (FIG. 4B). Similar results were obtained with Ang-II treatment, where it was found that Ang-II treatment significantly down regulated phospho-AMPK1-α levels and that co-incubation with Mito-Esc made cells resistant to Ang-II-mediated inhibition of phospho-AMPK1-α (FIG. 4C).

Example 5

Mito-Esc Treatment Increases Mitochondrial Biogenesis by Increasing SIRT-3, PGC-1A and TFAM Expressions—

Figure 5A:
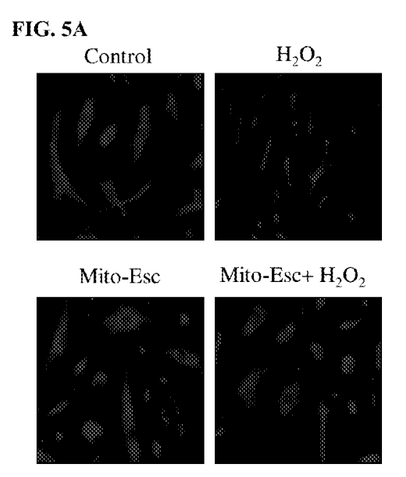
In FIG. 5A, cells were treated with $H_2O_2$ in the presence or absence of Mito-Esc for 8 h and mitochondrial staining was performed employing Mitotracker dye as described in the experimental section.
Figure 5B:
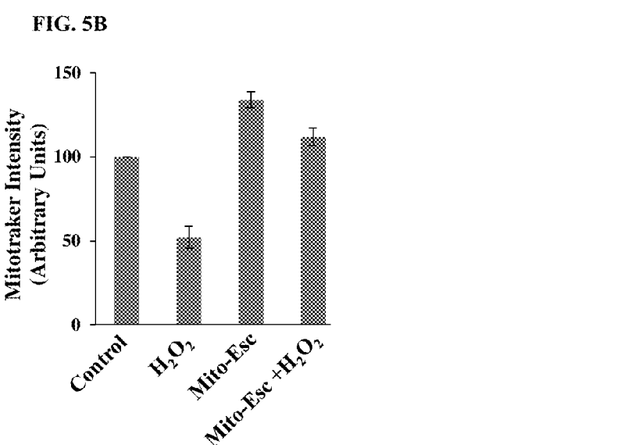
FIG. 5B shows the quantification of data shown in FIG. 5A by Image analysis software.
Figure 5C:
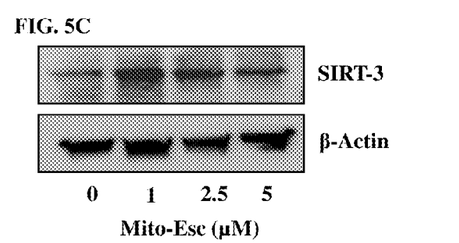
In FIG. 5C, HAEC were treated with various concentrations of Mito-Esc (1-5 µM) for 8 h and SIRT3 protein levels (marker of mitochondrial biogenesis) were measured by Western blot analysis.
Figure 5D:
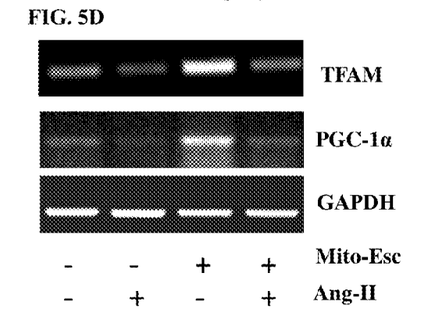
In FIG. 5D, cells were treated with Ang-II (500 nM) in the presence or absence of Mito-Esc (2.5 µM) for 8 h and RT-PCR was performed for TFAM and PGC-1α (markers of mitochondrial biogenesis) using gene specific primers.
Figure 5E:
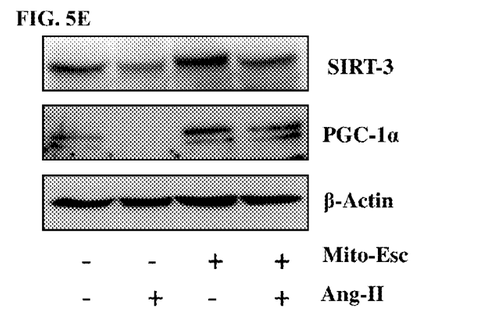
In FIG. 5E, cells were treated with Ang-II (500 nM) in the presence or absence of Mito-Esc (2.5 µM) for 8 h and SIRT3 and PGC-1α protein levels were measured by Western blot analysis.

To see if Mito-Esc treatment modulates oxidant-induced deregulation of mitochondrial biogenesis, we have treated HAEC with either $H_2O_2$ (500 µM) or Ang-II (500 nM) in the presence or absence of Mito-Esc (2.5 µM) or 8 h and then initially measured mitochondrial content using Mitotracker dye. It was found that Mito-Esc treatment significantly restored the oxidant-induced depletion of mitochondrial content (FIGS. 5A and B). In fact, mito-Esc treatment alone increased mitochondrial content when compared to control. Next we investigated the ability of Mito-Esc to modulate the mitochondrial biogenetic regulators namely, silent mating type information regulation 2 homolog (SIRT)-3, Peroxisome proliferator-activated receptor-gamma coactivator (PGC)-1α and mitochondrial transcription factor A (TFAM). It was found that Mito-Esc treatment (1-5 µM) significantly increased SIRT-3 levels in HAEC treated for 8 h (FIG. 5C). Similarly, Mito-Esc (2.5 µM) significantly increased both RNA and protein levels of PGC-1α, TFAM in cells treated for 8 h. Consistent with FIG. 5A, Mito-Esc treatment significantly reversed the Ang-II treatment induced inhibition of PGC-1A, TFAM and SIRT-3 levels (FIGS. 5D and E).

Example 6

Mito-Esc Delays Endothelial Cell Aging and Also Inhibits Oxidative Stress-Induced Cell Senescence—

Figure 6A:
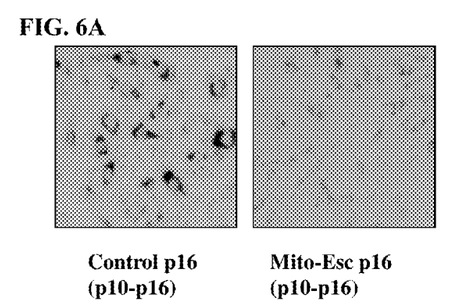
In FIG. 6A, HAEC were grown in the presence or absence of Mito-Esc (2.5 uM) for 6 passages/generations (P10 to P16) and then stained with senescence-associated b-Gal staining solution as described in the Experimental Section.
Figure 6B:
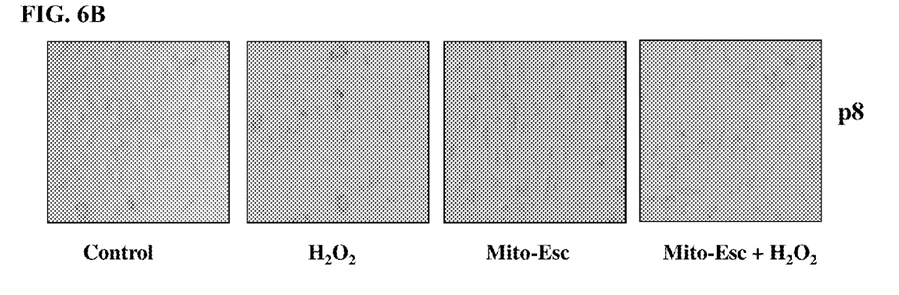
In FIG. 6B, cells (P8 passage, representing young cells) were treated with $H_2O_2$ (500 uM) in the presence or absence of Mito-Esc (2.5 µM) for 24 h and stained with senescence-associated b-Gal staining solution as described in the Experimental Section.

To study if Mti-Esc influences vascular aging; we have studied its effect on human aortic endothelial cell (HAEC) aging. For this, we used HAEC of different passages (representing different age) from P6 (young age) to P16 (old age). Also we have grown HAEC with Mito-Esc (2.5 µM) for six generations (six passages) to understand its chronic effects in regulating endothelial cell aging phenomenon. Results indicated that a chronic treatment of Mito-Esc greatly attenuated endothelial cell aging as evidenced by a significant reduction in the senescence-associated β-gal staining (FIG. 6 A). Thereby, suggesting that Mito-Esc treatment delays endothelial cell aging. Also, interestingly, Mito-Esc significantly inhibited $H_2O_2$-induced premature senescence in P6 (young age) HAEC (FIG. 6B).

Example 7

Mito-Esc Administration Attenuates the Incidence of Ang-II-Induced Aortic Aneurysm and Atheromatous Plaque Formation in ApoE$^{-/-}$ Mice—

Figure 7A:
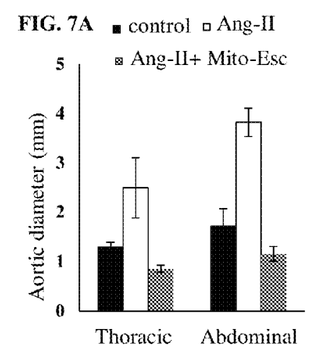
In FIG. 7A, thoracic and abdominal aortic diameters in control, Ang-II and Ang-II+ Mito-Esc treated groups. Animal experiment protocol is described in the Experimental Section.
Figure 7B:
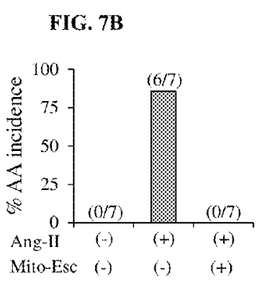
FIG. 7B represents percent aortic aneurysm incidence and, in FIG. 7C, percent plaque incidence.
Figure 7C:
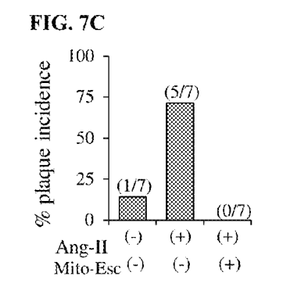
Figure 7D:
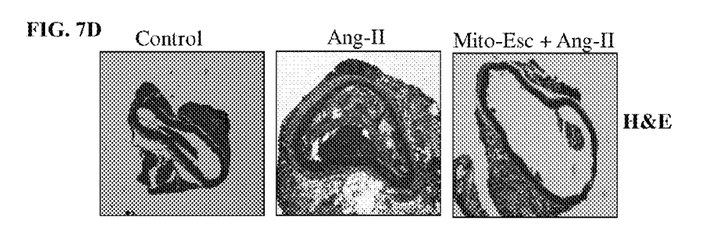
In FIG. 7D, histopathological images of aorta stained with Hemaoxylene & Eosin (showing the plaque formation) and, FIG. 7E, Mason-trichome (showing the fibrosis, blue color). Parenthesis indicates number of animals exhibited Aortic Aneurysm or plaque incidence.
Figure 7E:
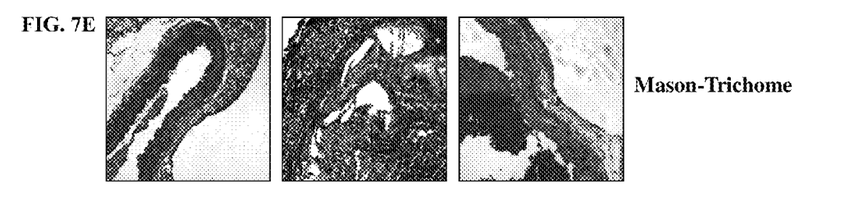
Figure 8A:
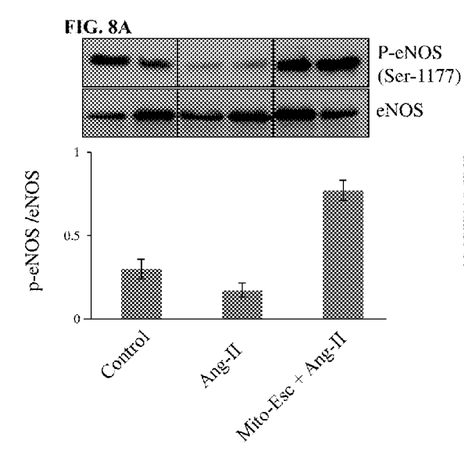
FIGS. 8A and 8B. Mito-Esc administration restores Ang-II induced inhibition of eNOS and AMPK phosphorylations in ApoE$^{-/-}$ mice aorta. eNOS and AMPK protein phosphorylation levels were measured in whole aortic tissue homogenates by Western blot analysis.
Figure 8B:
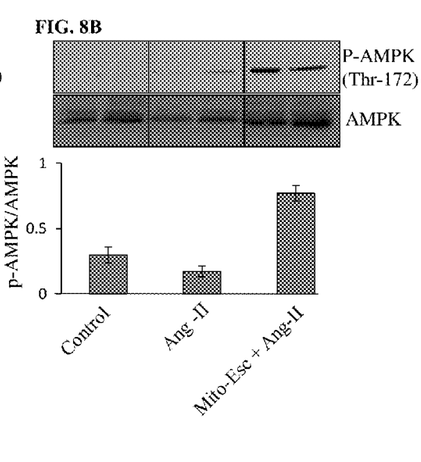
Figure 9A:
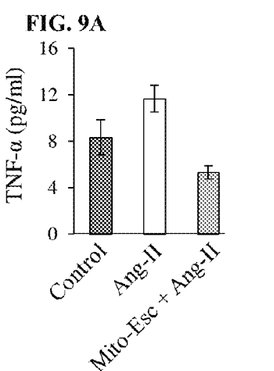
FIG. 9A, FIG. 9B, FIG. 9C, and FIG. 9D show the levels of serum tumor necrosis factor (TNF-α), interferon gamma (IFN-γ), macrophage colony stimulating factor-1 (MCP-1) and interleukin-6 (IL-6) respectively at the end of the 45 days animal protocol as described in the Experimental Section.
Figure 9B:
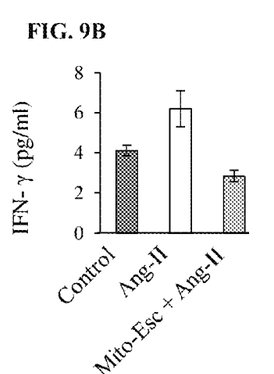
Figure 9C:
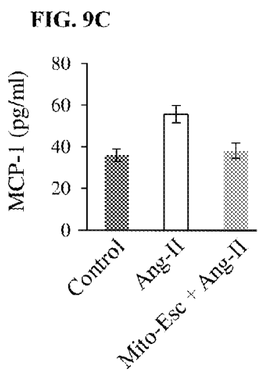
Figure 9D:
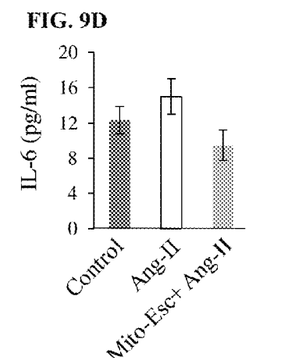
Figure 9E:
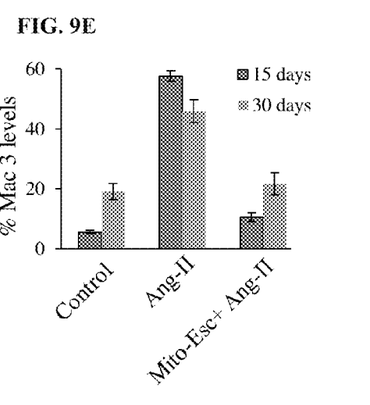
FIG. 9E shows the levels of Mac-3 (inflammatory macrophage marker) in serum at 15 and 30 days during the treatment protocol.

It is well documented that endothelial dysfunction is the most dominant risk factor for the development of vascular disorders including atherosclerosis. In relation to this, we have investigated the physiological significance of Mito-Esc in attenuating Ang-II-induced aortic aneurysm and atherogenesis in ApoE$^{-/-}$ mice model. Grossly, thoracic and abdominal aorta of Ang-II+Mito-Esc treated group showed a significant reduction in Ang-II-induced a) plaque extension, b) multiple numbers of micro/pseudo aneurysm formation and the c) maximal aortic diameters (FIGS. 7A, B and C) at the end of six weeks. These changes in Ang-II+Mito-Esc group were comparable to control group mice. We further analyzed the vascular remodelling employing histological stains in tissue sections of thoracic aortas. H&E staining of Ang-II+Mito-Esc treated group aorta showed a complete protection from Ang-II treatment alone induced severe atherosclerotic lesions with thick walls, intimal plaques. It was also noticed that the luminal diameter was significantly restored in Ang-II+Mito-Esc treated mice compared to Ang-II alone treated mice (FIG. 7D). Masson trichrome staining revealed thick fibrous mature connective tissue surrounding/in between atheroma in Ang-II treated mice aorta which was almost disappeared in Ang-II+Mito-Esc treated group (FIG. 7E). The collagen tissue in the atheroma, intimal, medial and external region appeared as blue color indicative of extensive proliferation of collagen tissue occurred in the atheromatous region of Ang-II treated mice. To further corroborate Mito-Esc's ability to protect from Ang-II-induced endothelial dysfunction during the progression of atheromatous plaque formation, we measured phospho-AMPK, AMPK, phospho-eNOS and eNOS protein levels in total aorta lysate. Intriguingly, Ang-II+Mito-Esc mice showed a significant increase in the phosphorylation statuses of both Enos and AMPK as compared to either Ang-II alone treatment or control groups (FIGS. 8A and B). These results are in agreement with cell culture results wherein, Mito-Esc treatment greatly increased phosphorylation of both eNOS and AMPK in HAEC. This suggests that Mito-Esc by increasing eNOS-derived nitric oxide generation restores endothelial function in Ang-II treated ApoE$^{-/-}$ mice. Along these lines, Ang-II+Mito-Esc treated mice showed a significant inhibition of Ang-II-induced proinflammatory cytokines (TNF-α, IFN-γ, MCP-1) production (FIGS. 9A-D). In tune with this, we have also measured Mac-3 levels by flow cytometry. Mac-3 is a general marker for macrophage abundance often seen under inflammatory conditions. Ang-II treatment greatly elevated Mac-3 levels by 30 days of treatment protocol, indicating an increased macrophage accumulation (FIG. 7G). However, Ang-II+ Mito-Esc group showed an inhibition of Mac3 levels during this time (FIG. 9E). Finally, to extend the vasculo-protective effects of Mito-Esc, it was observed that Mito-Esc treatment significantly reduced Ang-II mediated increase in the levels of LDL, VLDL, triglycerides and total cholesterol (Table 2). Also importantly, Mito-Esc treatment resulted in a significant rise in serum HDL levels (Table 2). Taken together, all these results implicate that Mito-Esc treatment significantly eases the incidence of vascular complications including plaque formation and aortic aneurysm.

TABLE 1

Cellular uptake of Esculetin and Mito-Esculetin

|  | Cytosolic fraction (nmol/mg protein) | Mitochondrial fraction (nmol/mg protein) |
|---|---|---|
| Esculetin (HAEC) | 6249 ± 235 | ND |
| Mito-Esc (HAEC) | 4488 ± 104 | 14523 ± 342 |
| Mito-Esc (Apo E$^{-/-}$ Mice Aorta) | ND | 2547 ± 286 |

ND indicates Not Detected

TABLE 2

Serum lipid profile of Apo E$^{-/-}$ mice treated with Ang-II alone or Ang-II + Mito-Esc for 45 days and serum lipid profile was measured

|  | Triglycerides (mg/dL) | LDL (mg/dL) | HDL (mg/dL) | VLDL (mg/dL) | Total Cholesterol (mg/dL) |
|---|---|---|---|---|---|
| Control | 175.33 ± 6.1 | 165.61 ± 15.6 | 23.58 ± 1.5 | 35.6 ± 0.7 | 364.51 ± 14.2 |
| Ang-II | 234.50 ± 21.5 | 423.93 ± 29.6 | 02.21 ± 1.2 | 46.9 ± 2.2 | 656.19 ± 34.2 |
| Mito-Esc + Ang-II | 150.74 ± 3.8 | 218.40 ± 20.9 | 45.53 ± 0.4 | 30.15 ± 0.4 | 414.85 ± 8.2 |

What is claimed is:
1. A process for the preparation of antioxidant compound F, said process comprising the steps of:
a) providing bromomethyl 9-bromononanoate as compound A and making a solution in dry THF at −75 to −80° C.;
b) providing a solution of t-butyl lithiate as compound B and mixing with THF under nitrogen atmosphere at −75 to −80° C. and adding a solution of LDA to the resulting mixture slowly for 1-2 hr;
c) adding the mixture obtained in step b) to compound A as obtained in step a) at −75 to −80° C. for 1-2 hr to obtain reaction mixture;
d) working up of the reaction mixture as obtained in step c) by quenching and extracting with ethylacetate to obtain organic extracts;
e) washing the organic extracts as obtained in step d) with water and drying over anhydrous Na$_2$SO$_4$ and filtering by known methods to give crude product, compound C as tert-butyl 11-bromo-3-oxoundecanoate;
f) adding benzene-1-2,4-triyl triacetate as compound D to compound C as obtained in step e) in H$_2$SO$_4$ at room temperature for 18-20 hr to obtain the reaction mixture;
g) working up of the reaction mixture as obtained in step f) by diluting with water and extracting with ethyl acetate to obtain organic extracts;
h) washing the organic extracts as obtained in step g with water and drying over anhydrous Na$_2$SO$_4$ and filtering and purifying by known methods to give crude compound E as 4-(8-bromooctyl)-6,7-dihydroxy-2H-chromen-2-one; and
i) mixing of compound E as obtained in step h) in DMF and triphenylphosphine to obtain a reaction mixture and heating the reaction mixture at 150-170° C. for 5-8 hr and further purifying by known methods to obtain the final product compound F as an esculetin analogue.

* * * * *